United States Patent [19]

Néel et al.

[11] Patent Number: 4,597,833
[45] Date of Patent: Jul. 1, 1986

[54] PROCESS FOR THE REMOVAL OF DISSOLVED GAS FROM AN AQUEOUS SOLUTION OF ETHYLENE OXIDE

[75] Inventors: Henri Néel, Le Havre; Francis Delannoy, Pierre-Benite, both of France

[73] Assignee: Atochem, France

[21] Appl. No.: 631,164

[22] Filed: Jul. 16, 1984

[30] Foreign Application Priority Data

Jan. 17, 1984 [FR] France ............... 84 00631

[51] Int. Cl.$^4$ ............... B01D 3/00; B01D 19/00
[52] U.S. Cl. ............... 203/49; 203/92; 203/96; 55/37; 55/53
[58] Field of Search ............... 203/49, 91, 92, 96, 203/68, 95; 549/538, 542; 568/867, 868; 55/51, 53, 47, 68, 44, 37; 159/DIG. 31

[56] References Cited

U.S. PATENT DOCUMENTS

| | | | |
|---|---|---|---|
| 2,771,473 | 11/1956 | Courter | 549/538 |
| 3,418,338 | 12/1968 | Gilman et al. | 203/4 |
| 3,729,899 | 5/1973 | Cunningham et al. | 55/51 |
| 3,922,314 | 11/1975 | Cocuzza et al. | 549/538 |
| 3,964,980 | 6/1976 | Ozero | 549/538 |
| 4,134,797 | 1/1979 | Ozero | 203/75 |
| 4,437,939 | 3/1984 | Bhise et al. | 203/68 |
| 4,469,492 | 2/1982 | Lagana et al. | 549/538 |

OTHER PUBLICATIONS

Chemical Abstracts, vol. 82, 1975, Snajdr et al., "Ethylene Stripping From Waste Gas in the Manufacture of Ethylene Oxide", p. 21.

Primary Examiner—S. Leon Bashore
Assistant Examiner—V. Manoharan
Attorney, Agent, or Firm—Sigalos & Levine

[57] ABSTRACT

A process for the removal of gases dissolved in an aqueous solution containing up to about 15% by weight of ethylene oxide and up to about 0.5% by weight of dissolved gases which are selected from carbon dioxide and at least one other compound that is normally gaseous, comprising contacting said aqueous solution of ethylene oxide with water and at least one gas selected from one of said dissolved normally gaseous compounds; other than carbon dioxide or oxygen, for a time and at a temperature and pressure sufficient to effect substantially complete removal of said dissolved gases; said contact taking place in a separation column having an upper and a lower zone and up to 15 theoretical placed in each zone with said aqueous solution of ethylene oxide being added intermediate said zones, said gas being added to the bottom of said lower zone, and said water being added to the top of the upper zone.

7 Claims, 1 Drawing Figure

PROCESS FOR THE REMOVAL OF DISSOLVED GAS FROM AN AQUEOUS SOLUTION OF ETHYLENE OXIDE

BACKGROUND OF THE INVENTION

The present invention concerns the treatment of dilute aqueous solutions of ethylene oxide containing dissolved gases in order to remove these gases from said solutions.

Such solutions can have various origins, but essentially originate from the synthesis of ethylene oxide by the catalytic oxidation of ethylene in the gaseous phase.

In such a synthesis, the ethylene oxide formed must be isolated from a gaseous mixture containing the ethylene oxide in a very dilute state and unconverted ethylene, unconverted oxygen, steam, carbon dioxide CO2, methane, ethane, nitrogen, rare gases and other impurities; the principal ones of which are aldehydes like formaldehyde and acetaldehyde.

The usual process to obtain the ethylene oxide from such a gaseous mixture comprises:

(a) Water absorption: The gaseous mixture originating from the reaction zone is placed in contact with water and a dilute aqueous solution of ethylene oxide is obtained containing about 2 to 3% of ethylene oxide by weight, impurities such as aldehydes and, in the dissolved state, particularly $CO_2$, methane, ethane, ethylene, nitrogen, oxygen and rare gases;

(b) Desorption: The dilute ethylene oxide solution is subjected to a steam extraction in a column delivering at the bottom an aqueous stream practically devoid of ethylene oxide and at the top a gaseous mixture containing steam gases initially dissolved in the aqueous solution of ethylene oxide, and impurities such as aldehydes and about 30 to 60% by weight of ethylene oxide;

(c) Reabsorption: The preceding gaseous stream, previously cooled, is placed in contact with water, ethylene oxide is reabsorbed as well as CO2 and the major part of the impurities, whereas the greatest part of the gases initially present in the dissolved form with the ethylene oxide are separated in the form of a gaseous stream. The aqueous ethylene oxide solution resulting from the reabsorption stage generally contains between 5 and 15% of ethylene oxide by weight; and (d) Distillation: The solution is then distilled in order to obtain pure ethylene oxide.

In addition, it is often necessary to insert a supplementary step between steps (c) and (d) in order to eliminate $CO_2$. The thus decarbonated aqueous solution of ethylene oxide can be treated in order to make glycols, distilled in order to obtain purified ethylene oxide, or partly treated in order to make glycols and partly distilled.

The object of the invention is the treatment of aqueous solutions such as those resulting from steps (a) and (c) of a procedure for the synthesis of ethylene oxide and, more generally, a procedure for all dilute aqueous solutions of ethylene oxide containing, in the dissolved state, carbon dioxide and at least one other compound normally gaseous and present in the solutions of the type cited originating from an ethylene oxide manufacturing procedure, in order to eliminate the dissolved gases directly from these solutions, in such a way that after their separation these gases can advantageously be recycled in the synthesis of ethylene oxide without carrying with them any ethylene oxide.

In fact, if such is not the case, it is necessary to proceed with a supplementary step in order to separate the ethylene oxide from these gases, prior to being able to recycle them in the synthesis of ethylene oxide.

Such a separation obviously complicates the general process for isolating the ethylene oxide and is not commercially feasible.

This is, for instance, a problem with the technique described in U.S. Pat. No. 3,729,899 which consists of subjecting the dilute ethylene oxide solution to a flash vaporization. Another drawback of this technique is that only a partial separation results, at the most equal to 85% of the gases initially dissolved in the treated ethylene oxide solution.

SUMMARY OF THE INVENTION

The present invention provides a process for the removal of dissolved gases practically devoid of ethylene oxide from an aqueous solution of ethylene oxide.

In brief, the present invention comprises a process for the removal of gases dissolved in an aqueous solution containing up to about 15% by weight of ethylene oxide and up to about 0.5% by weight of dissolved gases which are selected from carbon dioxide and at least one other compound what is normally gaseous, comprising contacting said aqueous solution of ethylene oxide with water and at least one gas selected from one of said dissolved normally gaseous compounds; other than carbon dioxide or oxygen, for a time and at a temperature and pressure sufficient to effect substantially complete removal of said dissolved gases; said contact taking place in a separation column having an upper and a lower zone and up to 15 theoretical plates in each zone with said aqueous solution of ethylene oxide being added intermediate said zones, said gas being added to the bottom of said lower zone, and said water being added to the top of the upper zone.

DETAILED DESCRIPTION

Figure 1:
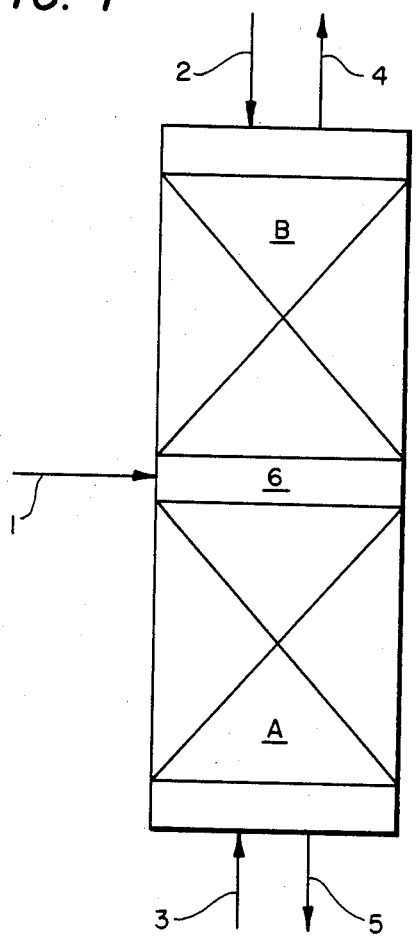
FIG. 1 is a schematic representation of an apparatus system suitable for carrying out the process of the present invention.

The column used can be any conventional separator column and the theoretical plates of the column can be any conventionally known; such as plates or packings, to ensure an effective gas-liquid contact.

Ideally, the absolute pressure in the column is between 1 and 20 bars.

The treated solution can contain up to 15% of ethylene oxide by weight. Most often it contains 2 to 12% of ethylene oxide by weight. The total amount of dissolved gases generally represents less than 0.5%, and most often less than 0.3% by weight of the solution.

The temperature of the ethylene oxide solution at its entrance into the column is generally above ambient temperature and below 80° C.

The water introduced at the top of the column can be pure water or water having been recycled in the ethylene oxide process and which can contain in particular small amounts of ethylene oxide and/or glycol. It can, for instance, be a water analogous to the one ensuring the absorption of ethylene oxide from the gases originating from the catalytic oxidation zone of the ethylene. Its temperature at its entrance into the column advantageously is between 10° C. and 50° C. Its flow rate is equal to 5 to 15% by weight of that of the ethylene oxide solution.

The gas stream introduced below the lower zone of the column advantageously consists of one or several gases selected from among nitrogen, ethylene, methane, ethane and argon. Its flow rate generally is between 0.05% and 10% by weight of the flow rate of the solution to be treated.

In the drawing, Column 6 includes two zones, A and B, comprising plates or packings, one containing at the most 15 theoretical plates.

The dilute aqueous ethylene oxide solution is introduced at 1 into the part of column 6 situated between zones A and B.

The gas stream serving to carry along the dissolved gases in the ethylene oxide solution is introduced at 3 into column 6, while water penetrates into this same column at 2.

At 4 a gas stream essentially consisting of gas initially dissolved in the ethylene oxide solution and of the gas or gases introduced at 3, is evacuated.

At 5 the treated ethylene oxide solution is evacuated.

The invention will be further illustrated in conjunction with the following examples, which are set forth for the purpose of illustration only and not by way of limitation.

EXAMPLE 1

An aqueous ethylene oxide solution containing, by weight, 2.55% of ethylene oxide, 5.22% of ethylene glycol, 0.17% of $CO_2$, 0.032% of ethylene, 0.015% of nitrogen and 0.004% of ethane, oxygen and argon overall, is introduced at a rate of 1902 kg/h and at 72° C. into column 6, whose two zones each have 5 theoretical plates.

The gas stream necessary in order to carry the dissolved gases along in the solution of ethylene oxide consists of nitrogen introduced into column 6 at a flow rate of 1.46 kg/h and at 25° C.

The aqueous stream introduced at the top of the column, consisting of water containing 5.5% of ethylene glycol by weight, is introduced into column 6 at a rate of 131.23 kg/h at 25° C.

The mean absolute pressure in column 6 is equal to 2.5 bars.

The gas stream evacuated at the top of the column at a rate of 5.66 kg/h contains 99.8% of the $CO_2$ and the entire amount of the other gases initially dissolved in the ethylene oxide solution introduced into the column. It contains less than 0.004% by weight of ethylene oxide.

The aqueous ethylene oxide solution evacuated at the bottom of the column at a flow rate of 2,029 kg/h only contains 0.003% by weight of dissolved $CO_2$. The coefficient of elimination of the $CO_2$ is over 98%.

An analogous result is obtained when the nitrogen is replaced by the same molar amount of methane.

EXAMPLE 2

By operating as in Example 1, but by utilizing a stream of ethylene at a rate of 1.91 kg/h in place of the nitrogen stream, the ethylene oxide solution evacuated at the bottom of the column contains only 1% of the $CO_2$ initially dissolved in the ethylene oxide solution introduced into the column, and only 0.01% by weight of ethylene.

The gas stream evacuated at the top of the column contains only 0.005% by weight of ethylene oxide.

EXAMPLE 3

By operating as in Example 2, but in a column only comprising 2 theoretical plates in the lower zone and with an ethylene flow rate of 3.76 kg/h, the yield of elimination of $CO_2$ reaches 99%, while the elimination of the other gases initially dissolved in the ethylene oxide solution introduced into the column is complete. The gas stream containing the gases eliminated from the ethylene oxide solution contains less than 0.015% by weight of ethylene oxide.

EXAMPLE 4

An aqueous solution containing by weight 2.5% of ethylene oxide, 0.17% of $CO_2$ and 0.32% of ethylene is introduced at a rate of 1902 kg/h and at 80° C. into column 6 whose 2 zones each have 5 theoretical plates and functioning under a mean absolute pressure of 15 bars. 19.4 kg/h of nitrogen at 25° C. and 131 kg/h of water at 25° C. are respectively introduced below the lower zone and above the upper zone of column 6.

The treatment according to the invention makes it possible to obtain a solution of ethylene oxide no longer containing but 1% of the initial $CO_2$, with the yield of overall elimination of the gases initially dissolved in the solution to be treated reaching 94% and the ethylene oxide content in the gas stream issuing at the top of the column being only 0.0005%.

EXAMPLE 5

An aqueous solution containing by weight 11.73% of ethylene oxide, 0.031% of $CO_2$ and 0.0014% of ethylene is introduced at 42° C. at a rate of 1971 kg/h into the column of Example 4 where it is placed in contact with a gaseous nitrogen stream introduced into this column at 25° C. at a rate of 3.83 kg/h.

Water is introduced at the top of the column at 25° C. at a flow rate of 131 kg/h.

The mean absolute pressure in the column is 2.5 bars.

The ethylene oxide solution extracted from the column contains less than 1% of the amount of $CO_2$ which it contained initially, with the elimination of the other dissolved gases being practically complete.

The gas stream extracted at the top of the column contains only 0.0003% by weight of ethylene oxide.

While the invention has been described in connection with a preferred embodiment, it is not intended to limit the scope of the invention to particular form set forth, but on the contrary, it is intended to cover such alternatives, modifications, and equivalents as may be included within the spirit and scope of the invention as defined by the appended claims.

What is claimed is:

1. A process for the removal of gases dissolved in an aqueous solution containing up to about 15% by weight of ethylene oxide and up to about 0.5% by weight of dissolved gases which are selected from carbon dioxide and at least one other compound that is normally gaseous, comprising contacting said aqueous solution of ethylene oxide with water and ethylene for a time and at a temperature and pressure sufficient to effect substantially complete removal of said dissolved gases; said contact taking place in a separation column having an upper and a lower zone and up to 15 theoretical plates in each zone with said aqueous solution of ethylene oxide being added intermediate said zones, said ethylene being added to the bottom of said lower zone, and said water being added to the top of the upper zone.

2. The process of claim 1, wherein the flow rate of the gas introduced into the column is between about 0.05% to 10% of the flow rate of the aqueous ethylene oxide solution introduced into the column.

3. The process of claim 1, wherein the temperature of the aqueous ethylene oxide solution is between about the ambient temperature and 80° C.

4. The process of claim 1, wherein the flow rate of the water introduced into the column is between about 5 to 15% of the flow rate of the aqueous ethylene oxide solution introduced into the column.

5. The process of claim 1, wherein the temperature of the water introduced into the column is between about 10° C. to 50° C.

6. The process of claim 1, wherein the mean absolute pressure in the column is between about 1 to 20 bars.

7. The process of claim 1, wherein the temperature of the aqueous ethylene oxide solution is between about the ambient temperature and 80° C., the flow rate of the gas is between about 0.05% to 10% of the flow rate of the aqueous ethylene oxide, the temperature of the water is between about 10° C. to 50° C. and the flow rate thereof is between about 5 to 15% of the flow rate of the aqueous ethylene oxide, and the column pressure is between about 1 to 20 bars.

* * * * *